US009636013B2

(12) United States Patent
Griggio, II

(10) Patent No.: US 9,636,013 B2
(45) Date of Patent: May 2, 2017

(54) OPHTHALMOSCOPIC APPARATUS

(71) Applicant: NEXT SIGHT S.R.L., Pordenone PN (IT)

(72) Inventor: Paola Griggio, II, Padua (IT)

(73) Assignee: NEXT SIGHT S.R.L., Pordenone PN (IT)

( * ) Notice: Subject to any disclaimer, the term of this patent is extended or adjusted under 35 U.S.C. 154(b) by 0 days.

(21) Appl. No.: 14/781,002

(22) PCT Filed: Mar. 28, 2014

(86) PCT No.: PCT/IT2014/000084
§ 371 (c)(1),
(2) Date: Sep. 28, 2015

(87) PCT Pub. No.: WO2014/155403
PCT Pub. Date: Oct. 2, 2014

(65) Prior Publication Data
US 2016/0045110 A1   Feb. 18, 2016

(30) Foreign Application Priority Data

Mar. 28, 2013  (IT) ................ VI2013A0088

(51) Int. Cl.
*A61B 3/14*  (2006.01)
*A61B 3/10*  (2006.01)
(Continued)

(52) U.S. Cl.
CPC .............. *A61B 3/12* (2013.01); *A61B 3/0083* (2013.01); *A61B 3/152* (2013.01); *A61B 3/154* (2013.01); *A61B 3/156* (2013.01); *G02B 27/281* (2013.01)

(58) Field of Classification Search
USPC ................................... 351/200–246
See application file for complete search history.

(56) References Cited

U.S. PATENT DOCUMENTS 7,306,336 B2 * 12/2007 Akita ............... A61B 3/0058
                                                351/205
2008/0165322 A1   7/2008 Su et al.
2013/0063698 A1 * 3/2013 Akiba ................. A61B 3/12
                                                351/206

FOREIGN PATENT DOCUMENTS

DE  102009009599 A1   8/2010
EP       2238890 A1  10/2010

OTHER PUBLICATIONS

Intrnational Search Report dated Aug. 26, 2014.
English Abstract for DE102009009599A1 dated Aug. 19, 2010.

* cited by examiner

*Primary Examiner* — Mohammed Hasan
(74) *Attorney, Agent, or Firm* — Hedman & Costigan, P.C.; James V. Costigan; Kathleen A. Costigan

(57) ABSTRACT

Ophthalmoscopic apparatus (10) having a frame (11) provided with references for the positioning of at least one of the user's eyes in an inspection position; a first optical unit (12) fixed to the frame (11) and faced to the inspection position references; a second optical unit (13) associated to the frame (11) and presenting an optical axis coincident with the optical axis of the first optical unit (12) and defining a main optical axis (A) incident in correspondence of the inspection position references; an image detecting device (14) fixed to the frame (11); a support (15) fixed to the frame (11) between the first optical unit (12) and the second optical unit (13), and having an operating part (B) permeable to the luminous radiation and intersected by the main optical axis (A); and a lighting means (16) associated to the support (15).

11 Claims, 2 Drawing Sheets

(51) Int. Cl.
*A61B 3/12* (2006.01)
*A61B 3/00* (2006.01)
*A61B 3/15* (2006.01)
*G02B 27/28* (2006.01)

OPHTHALMOSCOPIC APPARATUS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND OF THE INVENTION

1) Field of the Invention

The present finding refers to an ophthalmoscopic apparatus.

In particular, the present ophthalmoscopic apparatus falls within the category of apparatuses denominated fundus camera, i.e. it is suitable for vision and photographic reproduction of the eye fundus.

The present ophthalmoscopic apparatus is particularly suitable for vision and/or photographic reproduction of the retina.

Therefore the present invention falls in the optical devices field for eye inspection.

2) Description of Related Art

Nowadays, in the ophthalmoscopic apparatuses field, in particular, an ophthalmoscopic apparatus is known which is equipped with a controlling device employable by the operator to control the distance between the apparatus and the eye to be inspected.

This ophthalmoscopic apparatus comprises also a device for lighting the ocular fundus and a device comprising a detecting screen of ocular fundus image.

Furthermore, this ophthalmoscopic apparatus comprises focusing means for the focusing of ocular fundus on the screen.

In use, the ophthalmoscopic apparatus is placed in front of the eye to be inspected.

In detail, this ophthalmoscopic apparatus comprises a first optical unit and a second optical unit placed in front of the screen and which are aligned each other so to fix a main common optical axis of the ophthalmoscopic apparatus.

The second optical unit is placed between the screen and the first optical unit and is movable along the main optical axis for focusing the ocular fundus image on the screen.

The aforementioned controlling device comprises a luminous indicator placed between the first and the second optical unit and suitable for projecting, through the first optical unit, a luminous radiation towards the eye to be inspected.

The indicator image is reflected from the cornea on the detecting device screen by means of which it can be evaluated by an operator.

The controlling device is structured so that, if this reflected image is clear, then the ophthalmoscopic apparatus is at a right distance from the eye to be inspected, otherwise it is at a wrong distance.

This right distance is that distance where the indicator is conjugated with the eye pupil to be inspected in respect of the first optic unit.

The operator, thus, according to the aforementioned reflected image by the indicator, controls the ophthalmoscopic apparatus distance from the eye so to obtain the aforementioned right distance.

The indicator can consist of an only luminous signal or of a plurality of luminous signals circumferentially placed around the main optical axis.

The offset between such indicators image on the screen and the main optical axis gives the operator information for aligning the ophthalmoscopic apparatus with the eye to be inspected.

In fact, if the ophthalmoscopic apparatus is centred, i.e. is aligned with the eye to be inspected, the optical axis of this latter coincides with the main optical axis.

When the ophthalmoscopic apparatus is placed at the right distance from the eye and is centred on this one, means for focusing are operated which move the second optic unit so to obtain that ocular fundus and screen are conjugated.

Each indicator is realized by a first end of a light guide, in particular an optical fibre, the second end of the latter being in front of a lamp for receiving the luminous radiation.

Alternatively, the indicator can be realized by means of a specular surface on which a luminous radiation generated by a lamp is focused, by a lens, or by an optical unit, having an optical axis transverse to the main optical axis.

The light for lighting the ocular fundus is provided by the lighting device which traditionally comprises, in sequence, a lamp, a lens or an optical unit, and a mask conjugated to the lamp relative to the lens.

The lighting device has a secondary optical axis which intersects the main optical axis.

In correspondence of the intersection between the main and secondary optical axes, a mirror suitable for reflecting the lamp light towards the eye position, along the main optical axis, is placed.

Such mirror is perforated in the middle so as to allow the reflected light by the eye to pass, through the hole, towards the screen.

The mask, of the lighting device, has an annular slit suitable for making an annular beam of light generated by the lamp, such beam strikes peripherally the hole on the mirror.

The mask is conjugated to the eye pupil to be inspected when the ophthalmoscopic apparatus is placed at the aforementioned right distance from the eye, in which case the lamp light lightens the ocular fundus.

The focusing means comprise, further, an emitting device of infrared rays, suitable for lighting the ocular fundus.

The formed on the screen image by infrared light reflected from the ocular fundus, gives instructions for focusing on the screen the ocular fundus.

For the focusing, the second optical unit is moved along the main optical axis in order to have the infrared light image focused on the screen.

The focusing means comprise driving means suitable for jointly moving the second optical unit, along the main optical axis, and the infrared emitting device along the secondary optical axis.

This traditional ophthalmoscopic apparatus is structurally complex in particular because it provides that the lighting device extends transverse to the main optical axis and the infrared emitting device which has to be jointly moved with the second optical unit in order to allow the ocular fundus focusing.

A further reason of structural complexity is provided by the foreseen means for generating the indicator.

In fact the light guides, i.e. optical fibres, use requires a manual assembling and use of skilled operators to detriment to an easy and cheap production.

The known solution, in alternative to light guides, i.e. the lamp-lens-mirror unit, determines a size transversally to the main optical axis and the need of retaining such unit components each other correctly positioned.

Such structural complexity determines this traditional ophthalmoscopic apparatus to be complex to produce and also the maintenance of the same is complex, to detriment to its inexpensiveness.

The underlying problem of the present invention is to simplify this traditional ophthalmoscopic apparatus structure.

Main task of the present finding is of realizing an ophthalmoscopic apparatus that gives such problem a solution solving the before disclosed complained drawbacks of the ophthalmoscopic apparatus.

Into the scope of such task is an aim of the present finding to propose an ophthalmoscopic apparatus which, in comparison with the traditional one, has a less size in the transverse direction relative to the main optical axis.

Another aim of the present finding consists in realizing an ophthalmoscopic apparatus which uses fewer optical components, i.e. lenses or optical units, in comparison with the disclosed traditional ophthalmoscopic apparatus.

A further aim of the present finding consists in proposing an ophthalmoscopic apparatus which is of easier maintenance in comparison with the above disclosed traditional ophthalmoscopic apparatus.

BRIEF SUMMARY OF THE INVENTION

This task, as well as these other aims which will be more evident in the following are achieved by an ophthalmoscopic apparatus comprising a frame (11) provided with references for the positioning of at least one of the user's eyes in an inspection position;

a first optical unit (12) fixed to said frame (11) and faced to said inspection position;

a second optical unit (13) associated to said frame (11) and presenting an optical axis coincident with the optical axis of the first optical unit (12) and defining a main optical axis (A) incident in correspondence of said inspection position;

an image detecting device (14) fixed to said frame (11) and faced to said second optical unit (13), said second optical unit (13) comprising at least a lens (13a) movable along said main optical axis (A) for focusing the image of the user's ocular fundus on said image detecting device (14); characterized in that it comprises a support (15) fixed to said frame (11) between said first optical unit (12) and said second optical unit (13), and having an operating part (B) permeable to the luminous radiation and intersected by said main optical axis (A);

lighting means (16) associated to said support (15) for emitting a luminous radiation from peripheral positions to said operating part (B) towards said inspection position, for irradiating the user's eye to be inspected;

wherein said lighting means comprises led chips on board which are fixed to said support (15) in positions that are peripheral to said operating part (B) and circumferential to said main optical axis (A).

Detailed characteristics of the ophthalmoscopic apparatus according to this finding are reported in the dependent claims.

BRIEF DESCRIPTION OF THE SEVERAL VIEWS OF THE DRAWINGS

Further characteristics and advantages of this finding will be more evident from the description of a preferred embodiment, but not exclusive of the ophthalmoscopic apparatus according to this finding, explained by an indicative and not limitative way in the enclosed sheets of drawings, in which.

DETAILED DESCRIPTION OF THE INVENTION

Figure 1:
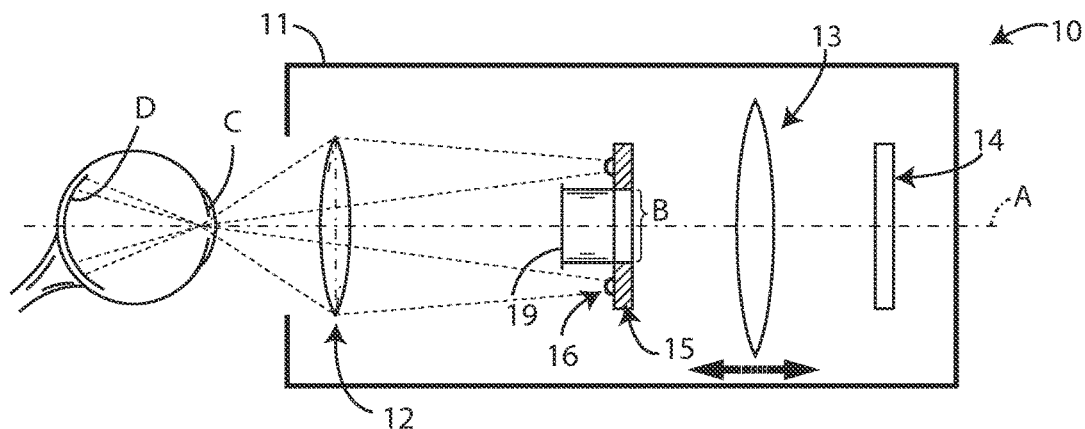
FIG. 1 illustrates a simplified scheme of an ophthalmoscopic apparatus according to this finding faced to a stylized eye to be inspected.

With particular reference to the mentioned figures, it is overall indicated by 10 an ophthalmoscopic apparatus suitable for vision and photographic reproduction of the ocular fundus.

The present ophthalmoscopic apparatus 10 is especially suitable for vision and/or photographic reproduction of the retina.

Structurally, the ophthalmoscopic apparatus 10 comprises a frame 11 provided with references for the positioning of at least one of the user's eyes in an inspection position.

Such references can consist of a face support, in case adjustable relative to the frame 11 and shaped so that the user, once has rested the face on the face support, presents his/her eye, or both eyes, in said inspection position.

The ophthalmoscopic apparatus 10 comprises also:

a first optical unit 12 fixed to the frame 11 and faced to said references of said inspection position;

a second optical unit 13 associated to the frame 11 and presenting an optical axis coincident with the optical axis of the first optical unit 12 and defining a main optical axis A incident in correspondence of said references of said inspection position;

an image detecting device 14 fixed to the frame 11 and faced to the second optical unit 13, preferably consisting of a CCD (acronym of the words: charge-coupled device) or CMOS (acronym of the words: complementary metal-oxide-semiconductor) detector.

The second optical unit 13 comprises at least a lens 13a movable along the main optical axis A for focusing the image of the user's ocular fundus on the image detecting device 14.

According to the finding, the ophthalmoscopic apparatus 10 presents a particular characteristic in that it comprises a support 15 fixed to the frame 11 between the first optical unit 12 and the second optical unit 13, and having an operating part B permeable to the light radiation and intersected by the main optical axis A;

lighting means 16 associated to the support 15 for emitting a luminous radiation from peripheral positions to the operating part B towards the inspection position references, for irradiating the eye to be inspected.

Preferably, the operating part B consists of a hole obtained on the support 15 and centred relative to the main optical axis A.

In alternative embodiments—all falling within the scope of the present finding—the operating part B may consist of a transparent part of the support 15.

The lighting means 16 advantageously comprise:

first lighting means 16a suitable for emitting a visible luminous radiation, i.e. having a wavelength less than 700 nm, for lighting the ocular fundus to be inspected;

second lighting means 16b suitable for emitting a luminous radiation in the field of the near-infrared i.e. having a wavelength comprised between 0.75 μm and 1.4 μm i.e. a frequency comprised between 400 THz and 214 THz, for irradiating the eye to be inspected without inducing the pupil constriction of the latter.

Preferably the lighting means comprise led chips on board and, advantageously, also collimating lenses, per se traditional and not illustrated in the enclosed figures, suitable for collimating the luminous radiation emitted by the led chips on board in a main emission direction.

Figure 4:
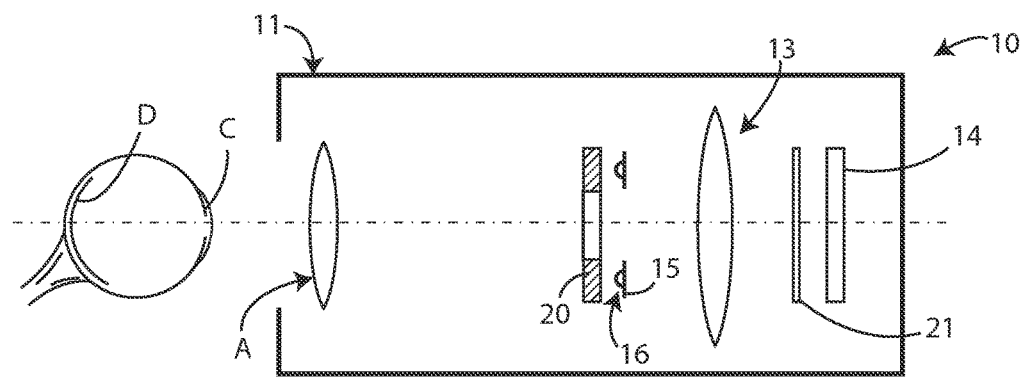
FIG. 4 illustrates an ophthalmoscopic apparatus variant of FIG. 1.

According to a first embodiment of the finding, illustrated in FIGS. 1 and 4, the led chips on board are advantageously fixed to the support 15 in positions peripheral to the operating part B and circumferential relative to the main optical axis A.

Advantageously, said led chips on board have an overall dimensions radius, on the support 15, comprised between 50 μm and 200 μm and they are putted near one other in order to form a ring coaxial with the main optical axis A.

The led chips on board forming the first lighting means 16a, advantageously are suitable for emitting light radiations corresponding to different colours and are preferably placed side by side with such a density to provide chromatic uniformity of the light, irradiated by them, which strikes the retina D.

The led chips on board forming the second lighting means 16b are preferably organized in two units, of which those forming a first unit are arranged together with, and in particular interposed to, the led chips on board forming the first lighting means 16a for emitting a near-infrared radiation suitable for continuously irradiating the ocular fundus for instance for filming the ocular fundus.

The chips on board forming the second of said units are arranged perimetrically to the operating part, for emitting a near-infrared radiation.

The radiation image of these chips on board of the second unit, reflected from the cornea and formed on the image detecting device 14 advantageously has the function of alignment index of the main optical axis A with the optical axis of the eye to be inspected.

Preferably the chips on board of the second unit have less distance from the operating part B relative to those of the first unit.

The ophthalmoscopic apparatus 10 advantageously comprises an electronic controlling device of said led chips on board which, in particular, may be programmed for feeding selectively a first half and, subsequently, a second half of the aforementioned ring formed by the led chips on board for allowing to form two stereographic images of the retina D.

According to the finding the first and second lighting means 16a and 16b can form two concentric rings or can be arranged, interposed to each other, to form a single ring.

Figure 2:
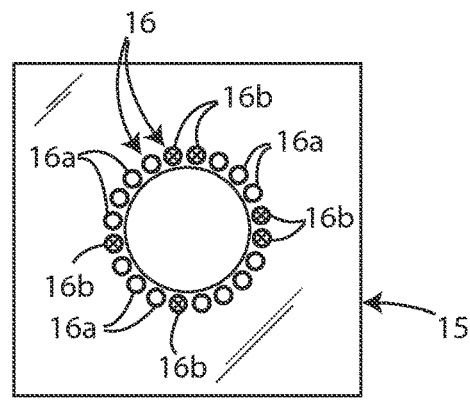
FIG. 2 illustrates a detail of the ophthalmoscopic apparatus of FIG. 1, related to the lighting means support.

In particular, the second lighting means 16b can be arranged to form discreet units around the operating part B, as illustrated for example in FIG. 2.

Figure 3:
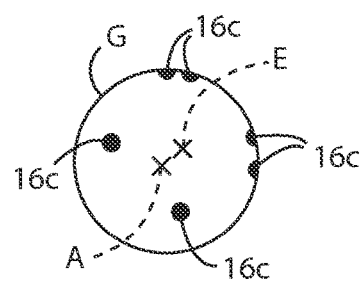
FIG. 3 illustrates a simplified scheme of an image by the first lighting means formed on the image detecting device of the ophthalmoscopic apparatus of FIG. 1, in case of a misalignment between the latter and the eye to be inspected.

In such case, the image of these discreet units will be reflected from the cornea on the image detecting device 14, on which it will be formed as illustrated for example in FIG. 3, where the images of the second lighting means 16b are designated by 16c.

In FIG. 3 the case is represented in which the optical axis to be inspected E is not coaxial with the main optical axis A.

In this case, the position of the images 16c relative to a reference G gives information to the operator about how repositioning the frame 11 relative to the eye to be inspected, for aligning the optical axis of the eye to be inspected E when it is not coaxial with the main optical axis A.

To this purpose advantageously the frame 11 is integrated in an optical head, movable relative to said references of said inspection position of the eye. Preferably are provided driving means adapted to the moving of such optical head, electronically controlled and automatically operated by said electronic controlling device.

Figure 5:
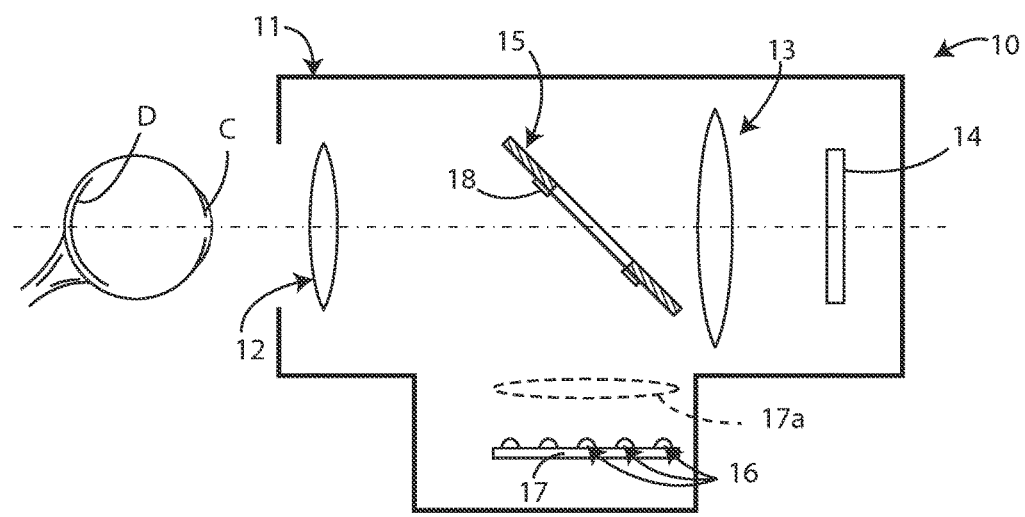
FIG. 5 illustrates a further ophthalmoscopic apparatus variant of FIG. 1.

In a second embodiment of the finding, illustrated in FIG. 5, the lighting means 16 advantageously comprise:

a backing 17 fixed to the frame 11, to which are fixed the led chips on board, these are faced to the support 15 for emitting towards it a luminous radiation;

a specular surface 18, forming part of the lighting means 16 and fixed to or integrated with the support 15, peripheral to the operating part B and suitable for reflecting a luminous radiation emitted by said led chips on board towards said references of said inspection position.

Advantageously, according to the present embodiment, a focalization lens 17a is also provided suitable for focalizing, on the specular surface 18, the radiation emitted by the lighting means 16.

Preferably, the ophthalmoscopic apparatus 10 comprises a conic or cylindrical optical stop 19, fixed to the support 15 and coaxial with the main optical axis A, suitable for, at least partially, shielding the light emitted by the led chips on board towards the main optical axis A.

This optical stop 19 advantageously projects from the support 15 towards the references of said inspection position.

The ophthalmoscopic apparatus 10 according to the finding advantageously comprises also means of optical filtering, connected to the image detecting device 14 and suitable for shielding the image detecting device 14 from visible light not coming from the fundus of the eye to be inspected.

These means of optical filtering preferably comprise:

a first polarizing filter 20 having a first polarizing direction, placed opposite to the lighting means 16 for polarizing the luminous radiation emitted by them;

a second polarizing filter 21 having a second polarizing direction which is perpendicular to said first polarizing direction, such second polarizing filter 21 being placed opposite to the image detecting device 14 for shielding the latter from luminous, visible, radiations, which present said first polarizing direction.

The means of optical filtering advantageously are suitable for shielding the image detecting device 14 from infrared light which does not come from the fundus of the eye to be inspected, to allow infrared filming and/or infrared photographs of the ocular fundus.

Preferably the polarizing filters 20 and 21 have:

an high extinction ratio in relation to the wavelengths of the visible light and a low extinction ratio in relation to the wavelengths of the near infra-red, for allowing an effective use of the lighting means 16 both for the lighting of the retina D of the eye to be inspected by visible light and by near infra-red radiation for the alignment of the optical axis of the eye E with the main optical axis A.

Alternatively to polarizing filters 20 and 21 a single linear polarizer with, in succession, a thin plate at λ/4, both not perforated in correspondence of the operating part B can be provided.

Operationally, when the ophthalmoscopic device is correctly placed relative to the eye to be inspected, i.e. the eye is in the aforementioned inspection position, the lighting means 16 are in a position conjugated with the pupil C relative to the first optical unit 12.

The second optical unit 13 advantageously comprises one or more lenses movable along the main optical axis for compensating a possible myopia or hypermetropia of the eye during the focusing of the retina D.

An ophthalmoscopic apparatus according to the present finding achieves thus the aforementioned task and aims allowing in particular to realize an ophthalmoscopic apparatus structurally simpler than the traditional ophthalmoscopic apparatuses.

Furthermore, an ophthalmoscopic apparatus according to the finding has a smaller size in the transversal direction relative to the main optical axis, relative to the traditional ophthalmoscopic apparatuses, and allows employing fewer optical components, i.e. lenses or optical units, all to the advantage of the simplicity of assembly, of maintenance and so of the overall production and management costs.

An ophtalmoscopic apparatus according to the finding presents also the advantage of having fewer movable components relative to the traditional ones, thus reducing the risk of malfunctions or breakdowns.

A further advantage of the ophtalmoscopic device according to the present finding, relative to the traditional ones is that it avoids the employment of the optical fibres, which are expensive and of complex management, allowing also to integrate in a single component, the support equipped with the first and second lighting means, the function of lighting the retina and of forming luminous, near infra-red, signals on the same for the alignment of the main optical axis to the optical axis of the eye.

An ophtalmoscopic apparatus according to the finding is easily assemblable and allows avoiding complicated calibrations thanks to the fact of providing the first lighting means and the second lighting means coaxial to the main optical axis.

The finding so conceived is susceptible of numerous modifications and variants, all falling within the scope of protection of the enclosed claims.

Furthermore, all details may be replaced by other technically equivalent elements.

In practice, the employed materials, as well as the contingent shapes and sizes, may be changed according to the contingent requirements and the state of the art.

Where the structural characteristics and the techniques mentioned in the following claims are followed by marks or numbers of reference, such marks or numbers of reference have been affixed with the only aim of increasing the intelligibility of the claims themselves and, accordingly, they do not represent in any way a limitation to the interpretation of each element identified, merely by way of example, by such marks or numbers of reference.

The invention claimed is:

1. Ophthalmoscopic apparatus comprising
   a frame provided with references for the positioning of at least one of the user's eyes in an inspection position;
   a first optical unit having an optical axis, said first optical unit being fixed to said frame and faced to said inspection position;
   a second optical unit associated to said frame and presenting an optical axis coincident with the optical axis of the first optical unit and defining a main optical axis (A) incident in correspondence of said inspection position;
   an image detecting device fixed to said frame and faced to said second optical unit, said second optical unit comprising at least a lens movable along said main optical axis (A) for focusing the image of the user's ocular fundus on said image detecting device;
   characterized in that it comprises
   a support fixed to said frame between said first optical unit and said second optical unit, and having an operating part (B) permeable to the luminous radiation and intersected by said main optical axis (A);
   lighting means associated to said support for emitting a luminous radiation from peripheral positions to said operating part (B) towards said inspection position, for irradiating the user's eye to be inspected
   said lighting means comprising led chips fixed to said support in positions that are peripheral to said operating part (B) and circumferential to said main optical axis (A).

2. Ophthalmoscopic apparatus according to claim 1 characterized in that said lighting means comprise:
   first lighting means suitable for emitting a visible luminous radiation for lighting the ocular fundus to be inspected;
   second lighting means suitable for emitting a luminous radiation in the near-infrared field for irradiating the eye to be inspected without inducing a pupil constriction of the latter.

3. Ophthalmoscopic apparatus according to claim 1, characterized in that said lighting means comprise collimating lenses suitable for collimating the luminous radiation emitted by said led chips on board in a main emission direction.

4. Ophthalmoscopic apparatus according to claim 3 characterized in that said led chips on board are fixed to said support in positions peripheral to said operating part (B) and circumferential to said main optical axis (A).

5. Ophthalmoscopic apparatus according to claim 3 characterized in that said lighting means comprise:
   a backing fixed to said frame, said led chips on board being fixed to said backing which are faced to said support for emitting towards it a luminous radiation;
   a specular surface, forming part of the lighting means and fixed on or integrated with said support, said specular surface being peripheral to said operating part (B) and suitable for reflecting a luminous radiation emitted by said led chips on board towards said inspection position.

6. Ophthalmoscopic apparatus according to claim 1, characterized in that said lighting means comprise: —a backing fixed to said frame, said led chips on board being fixed to said backing which are faced to said support for emitting towards it a luminous radiation; —a specular surface, forming part of the lighting means and fixed on or integrated with said support, said specular surface being peripheral to said operating part (B) and suitable for reflecting a luminous radiation emitted by said led chips on board towards said inspection position.

7. Ophthalmoscopic apparatus according to claim 1, characterized in that it comprises a conic or cylindrical optical stop fixed to said support coaxial with said main optical axis (A) and projecting from said support towards said inspection position to partially shield the light emitted by said led chips on board towards said main optical axis A.

8. Ophthalmoscopic apparatus according to claim 1 characterized in that it comprises means of optical filtering, connected to said image detecting device and suitable for shielding said image detecting device from visible light not coming from the fundus of the eye to be inspected.

9. Ophthalmoscopic apparatus according to claim 8, characterized in that said means of optical filtering comprise:

a first polarizing filter having a first polarizing direction, placed opposite to said lighting means for polarizing the luminous radiation emitted by them;

a second polarizing filter having a second polarizing direction perpendicular to said first polarizing direction, placed opposite to said image detecting device for shielding the latter from a luminous, visible, radiation having said first polarizing direction.

10. Ophthalmoscopic apparatus according to claim 9, characterized in that said means of optical filtering are suitable for shielding said image detecting device from infrared light not coming from the fundus of the eye to be inspected.

11. Ophthalmoscopic apparatus according to claim 8, characterized in that said means of optical filtering are suitable for shielding said image detecting device from infrared light not coming from the fundus of the eye to be inspected.

* * * * *